United States Patent [19]

Graf

[11] Patent Number: 5,329,933
[45] Date of Patent: Jul. 19, 1994

[54] DEVICE FOR MEASURING THE ANGLE OF MOVEMENT OF TWO VERTEBRAE

[76] Inventor: Henry Graf, 8, rue Duquesne, Lyons, France, 69006

[21] Appl. No.: 56,872

[22] Filed: May 5, 1993

Related U.S. Application Data

[62] Division of Ser. No. 950,632, Sep. 14, 1992, Pat. No. 5,291,901.

Foreign Application Priority Data

Sep. 24, 1991 [FR] France .................. 91 11964

[51] Int. Cl.⁵ ............................................. A61B 5/103
[52] U.S. Cl. ...................................... 128/781; 128/782; 33/512
[58] Field of Search ..................... 128/782, 781, 774; 33/512, 511, 513, 514, 515

[56] References Cited

U.S. PATENT DOCUMENTS

| | | | |
|---|---|---|---|
| 2,532,915 | 12/1950 | Horner | 128/781 |
| 3,271,868 | 9/1966 | Kuntscher et al. | 33/512 |
| 3,815,247 | 6/1974 | Debrunner | 33/512 |
| 4,461,085 | 7/1984 | Dewer et al. | 33/512 |
| 4,665,928 | 5/1987 | Linial et al. | 128/782 |
| 4,730,625 | 3/1988 | Fraser et al. | 128/781 |
| 4,800,897 | 1/1989 | Nilsson | 128/782 |
| 4,872,268 | 10/1989 | Perrault | 33/512 |
| 4,986,280 | 1/1991 | Marcus et al. | 128/774 |
| 5,012,819 | 5/1991 | Marras et al. | 128/781 |
| 5,188,121 | 2/1993 | Hanson | 128/781 |

FOREIGN PATENT DOCUMENTS

| | | | |
|---|---|---|---|
| 1531671 | 5/1968 | France | 128/781 |
| 9011720 | 10/1990 | PCT Int'l Appl. | 128/781 |
| 1103849 | 7/1984 | U.S.S.R. | 128/781 |
| 1623613 | 1/1991 | U.S.S.R. | 128/781 |

OTHER PUBLICATIONS

Panjabi et al. "A Technique for Measurement . . . to the Human Spine" Journal of Biomechanics, vol. 14, No. 7, pp. 447–460 (1981).

Houge et al "Gage for Evaluating Rheumatoid Hands" NASA Tech Briefs, vol. 5, No. 4, Mar. 1980, p. 461.

*Primary Examiner*—Stephen C. Pellegrino
*Assistant Examiner*—Guy V. Tucker
*Attorney, Agent, or Firm*—Dowell & Dowell

[57] ABSTRACT

A device for measuring angles of freedom of adjacent vertebrae which includes two reference elements associated with each vertebra respectively. Indicators are associated with the two reference elements for measuring the angle of freedom of movement of the vertebrae in torsion in a plane perpendicular to the longitudinal axis of the vertebrae and for measuring the angle of freedom of the vertebrae in lateral inflexion in a plane perpendicular to that of the spinous processes as a function of a given position of flexion-extension of the vertebrae in the plane containing the spinous processes.

1 Claim, 6 Drawing Sheets

DEVICE FOR MEASURING THE ANGLE OF MOVEMENT OF TWO VERTEBRAE

This application is a division, of application Ser. No. 07/950,632, filed Sep. 14, 1992, now U.S. Pat. No. 5,291,901.

BACKGROUND OF THE INVENTION

Field of the Invention

The present invention relates to a device intended to measure, on the one hand, the angle of freedom of two adjacent vertebrae in torsion and, on the other hand, the angle of freedom of these vertebrae in lateral inflexion with respect to a given position in flexion-extension of the vertebrae.

HISTORY OF THE RELATED ART

In theory, it is considered that the intervertebral articulation comprises 6° of freedom, but, in practice, the principal freedom of the articulation lies in flexion-extension. Similarly, but to a lesser amplitude, there exist degrees of freedom upon intervertebral horizontal rotation or lateral flexion.

It should also be noted that these two movements are usually linked with each other, i.e. the lateral flexion necessarily causes a certain horizontal degree of rotation, and vice versa.

The problem of this lumbar intervertebral articulation is that it is rapidly subject to damage, leading to a reduction in the rubbery quality of the disc. Such deterioration results in a greater suppleness of the articulation, which brings about more ample movements both in flexion-extension, but also in lateral inflexion and in torsion.

The reduction in the rubbery quality of the disc leads to a complete disorganization of the movements of the lumbar intervertebral articulation.

It therefore seems important, for certain therapeutical decisions, both to be able to measure the amplitude of all the intervertebral movements and to have an idea of the disorganization of the coupling of the movements with respect to one another.

It is a particular object of the present invention to provide a solution to this problem.

SUMMARY OF THE INVENTION

The purpose of the present invention is to design a measuring device capable of indicating, at any moment and in any position, the three-dimensional rotations of one vertebra with respect to the other. This device makes it possible in particular to assess the movements of intervertebral inflexion and rotation at certain places of the intervertebral flexion-extension.

The measurements obtained by this device will make it possible to take decisions for certain therapeutical positions, and this "in vivo", during operations. The measuring device may be used outside surgery, abutting percutaneously on the intervertebral spines. During an operation, the measuring device will abut on screws which will be placed in the pedicles of the vertebra.

The device according to the invention for measuring the amplitudes of two vertebrae comprises two reference elements rigidly associated respectively with each vertebra, means associated with two reference elements for measuring the angle of freedom of the vertebra considered in torsion, i.e. in a plane perpendicular to the longitudinal axis of these vertebrae, and other means associated with such elements for measuring the angle of freedom of the vertebrae in lateral inflexion, i.e. in a plane perpendicular to that of the spinous processes as a function of a given position in flexion-extension of the vertebrae, i.e. in the plane containing the spinous processes.

BRIEF DESCRIPTION OF THE DRAWINGS

The invention will be more readily understood on reading the following description with reference to the accompanying drawings, in which.

DESCRIPTION OF THE PREFERRED EMBODIMENTS

Figure 1:
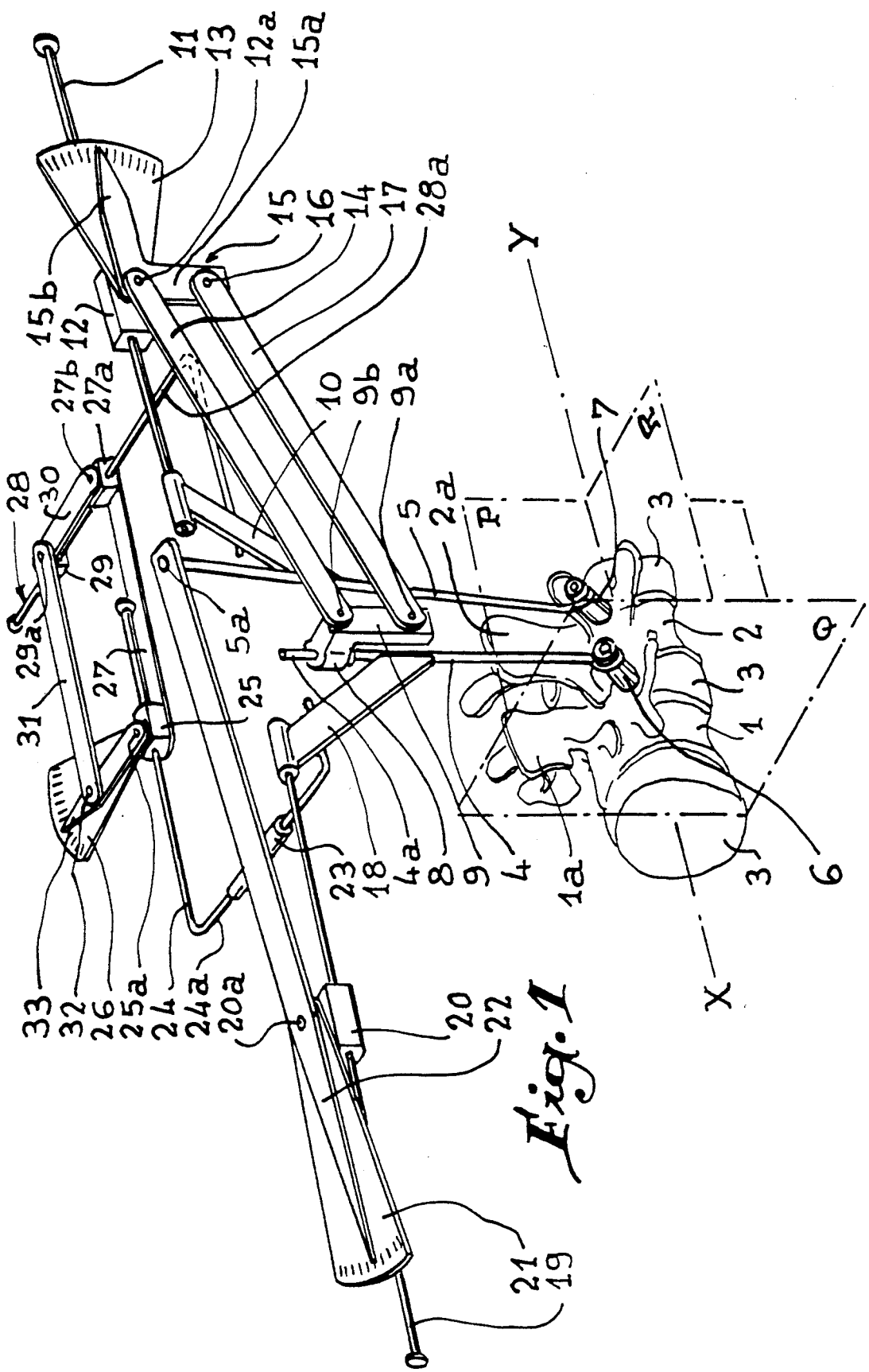
FIG. 1 is a perspective view of the device according to the invention.

Referring now to the drawings, FIG. 1 illustrates two adjacent vertebrae 1, 2 separated in conventional manner by a disc 3. X-Y designates the longitudinal axis of the vertebrae and a plane P containing this axis is shown, as well as the spinous processes 1a, 2a of the vertebrae 1 and 2. This Figure also shows a transverse plane Q passing through the disc 3 and orthogonal with respect to the axis X, Y as well as to plane P. A third plane R containing axis X, Y has also been shown in FIG. 1, its orientation being orthogonal with respect to the two planes P and Q.

In the following specification, the term flexion-extension will designate the movement of the vertebrae in position, for example, of cyphosis in which the axis X-Y becomes curved while remaining in plane P. The term torsion will designate the rotation of one vertebra with respect to the other planes parallel to plane Q. Finally, lateral inflexion will designate the movement of the vertebrae with respect to each other such that axis X-Y becomes curved while remaining in plane R.

The device according to the invention firstly comprises two small rods 4, 5 of which one of the ends is respectively fixed to each of the vertebrae 1 and 2 by any appropriate means, for example implants or screws 6, 7. The two small rods rise slightly obliquely in order that the free end of column 4 is offset laterally with respect to plane P whose trace has been shown in FIG. 2, while the free end of column 5 is virtually contained in this plane.

The free end of rod 4 comprises an endpiece 4a of smaller diameter, which engages freely in a hole of a block 8 having a small bar 9 extending parallel to column 4. This bar includes two pivots 9a, 9b.

Figure 2:
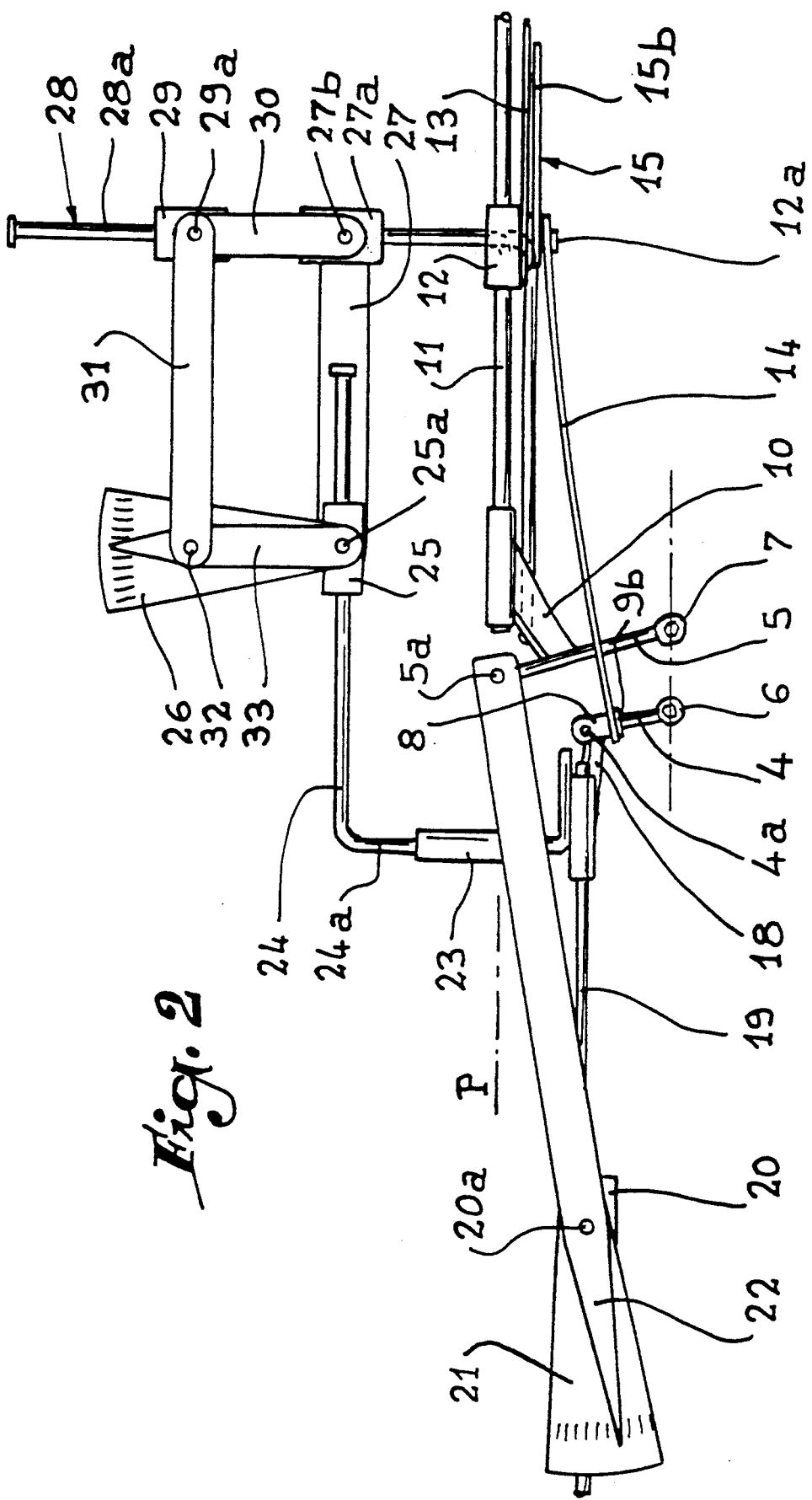
FIG. 2 is a plan view of this device.

The upper part of rod 5 is secured to an oblique flat section 10 to which is secured a rod 11 extending substantially parallel to axis P (cf. FIG. 2). On this rod is mounted to slide freely a carriage 12 to which is secured a segment of circle forming dial 13 which is suitably graduated and parallel to plane P. On its lateral face, the carriage 12 includes a pivot 12a parallel to those 9a, 9b of bar 9. A supple connecting rod 14 is articulated on pivots 9b, 12a. About the latter pivots the apex of a square bracket 15 of which one, 15a, of the arms, parallel to bar 9 and of the same length, is provided with a pivot pin 16 for one of the ends of a supple connecting rod 17 of which the other end is articulated on pivot 9a. The other arm 15b of the square bracket 15 constitutes a needle which moves in front of the graduated portion of the dial 13. The two connecting rods 14, 17, the bar 9 and the arm 15a of the needle 15 form a deformable parallelogram linkage.

The upper part of the column 4 located immediately below the block 8 is provided with an oblique flat section 18 secured to a rod 19 extending perpendicularly to rod 4 and virtually parallel to rod 11, as illustrated in FIG. 2. A carriage 20 is mounted to slide freely along rod 19. This carriage bears a suitably graduated dial 21 disposed parallel to plane R as well as a pin 20a about which is articulated a needle 22 of which the end opposite that located in front of the graduation of dial 21 is articulated about the free end 5a of rod 5.

A bearing 23, substantially parallel to plane R, is fixed to section 18, its orientation being perpendicular to the plane formed by rod 4 and rod 19. In this bearing is mounted for free rotation the end of one of the arms 24a of a square-bent rod 24 of which the second arm, parallel to rod 19, receives for free sliding movement a block 25 bearing a graduated dial 26 oriented substantially parallel to plane R. This block is also secured to one of the ends of a bar 27 of which the other end includes a head 27a traversed for free sliding movement by a rod 28 secured to the second rod 5. Rod 28 presents the form of a square bracket of which the arm 28a which cooperates with the head 27a is perpendicular to the plane determined by the rod 5 and the rod 11. The arm 28a of the rod 28 is freely slidable with respect to a block 29. The latter, the block 25 and the head 27a respectively carry pivots 29a, 25a and 27b. Between pivots 27b and 29a is mounted a lever 30. A lever 31 is articulated by one of its ends on pivot 29a and by its other end on a pin 32 a needle 33 of which the end opposite its indicator part is articulated about pivot 25a. In this way, the bar 27, the levers 30 and 31 and the needle 33 form a deformable parallelogram.

Figure 3:
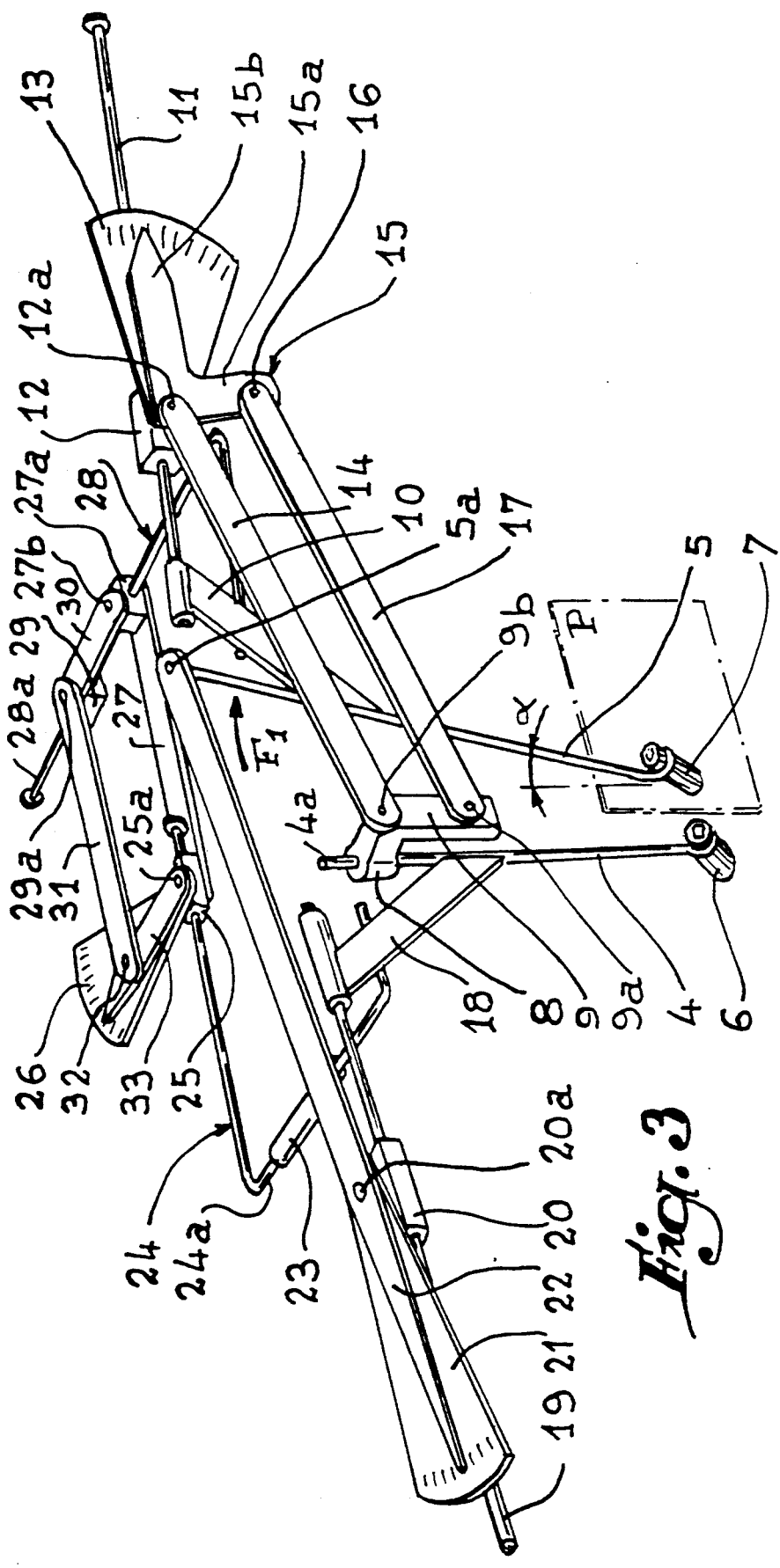
FIG. 3 is a view similar to that of FIG. 1, but Illustrating two adjacent vertebrae displaced angularly with respect to each other in the sense of a cyphosis.
Figure 4:
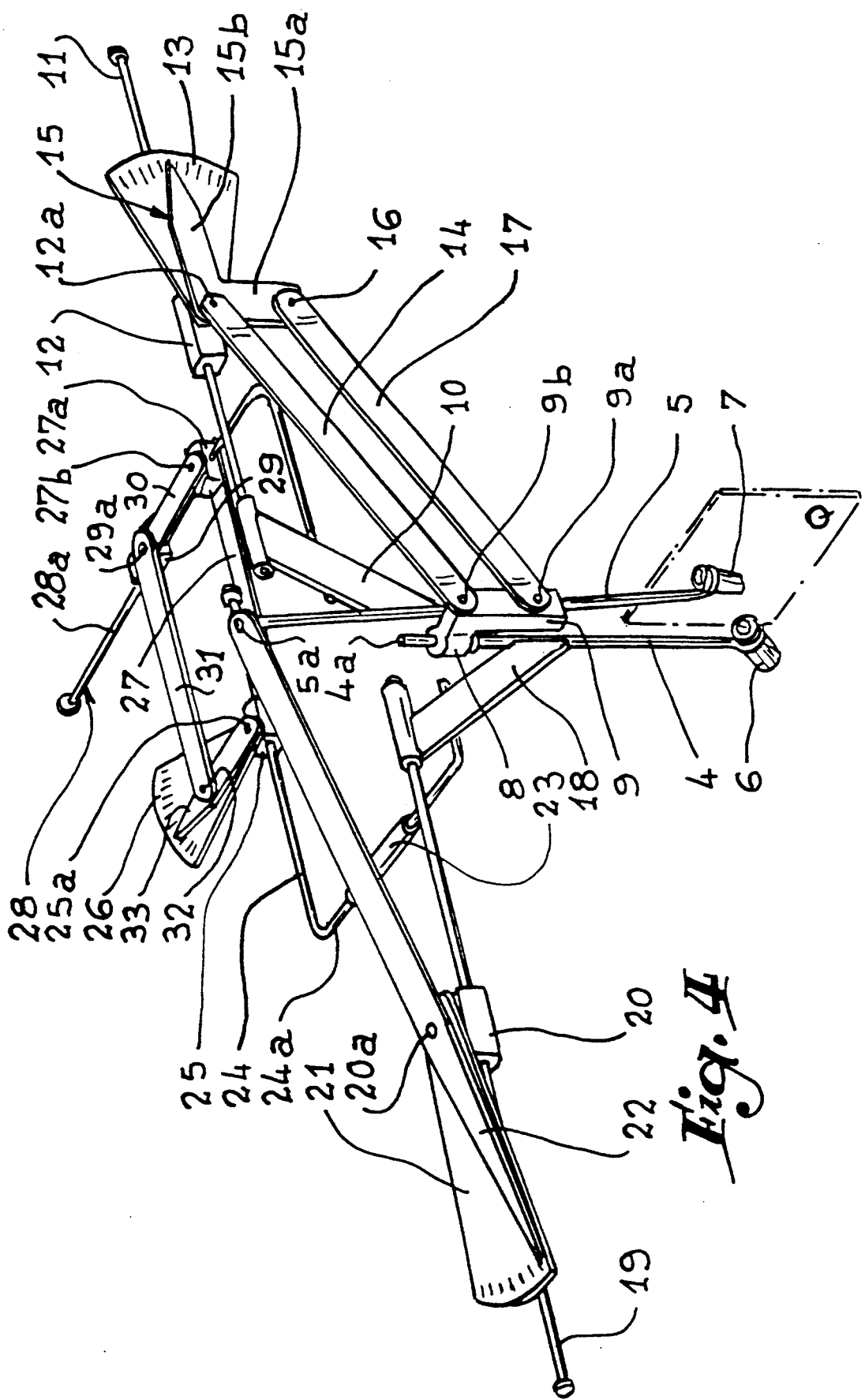
FIG. 4 shows the measurement of the angle of twist of the two vertebrae from their position illustrated in FIG. 3.

Operation is as follows: during the measurement of the amplitude of the clearance of the two vertebrae 1 and 2 in the sense of flexion-extension, the curvature of the vertebrae in this sense creates an angle α (FIG. 3) between rods 4 and 5, so that the end 5a of rod 5 moves away from that, 4a, of rod 4 (arrow $F_1$), with the columns being displaced in planes parallel to plane P. Such displacement provokes a movement of the carriage 12 along the rod 11, so that the deformable parallelogram formed by bar 9, the two supple rods 14, 17 and the arm 15a of the needle 15 is deformed, bringing about the displacement of the end of the needle 15 with respect to the graduation of the dial 13 to indicate the value of the angle α. Of course, this displacement also causes the carriage 20 to slide with respect to rod 19, but without noteworthy modification of the position of the needle 22. Simultaneously, the rod 28 tips in the direction of the vertebrae, which provokes a rotation of the rod 24 in the bearing 23. Due to the parallelism between rods 11 and 19, the position of the needle 33 with respect to the graduation of the dial 26 does not visibly vary.

From any relative position of flexion-extension of the two vertebrae 1 and 2, it is possible to measure the amplitudes in rotation and in lateral inflexion of the two vertebrae.

Figure 5:
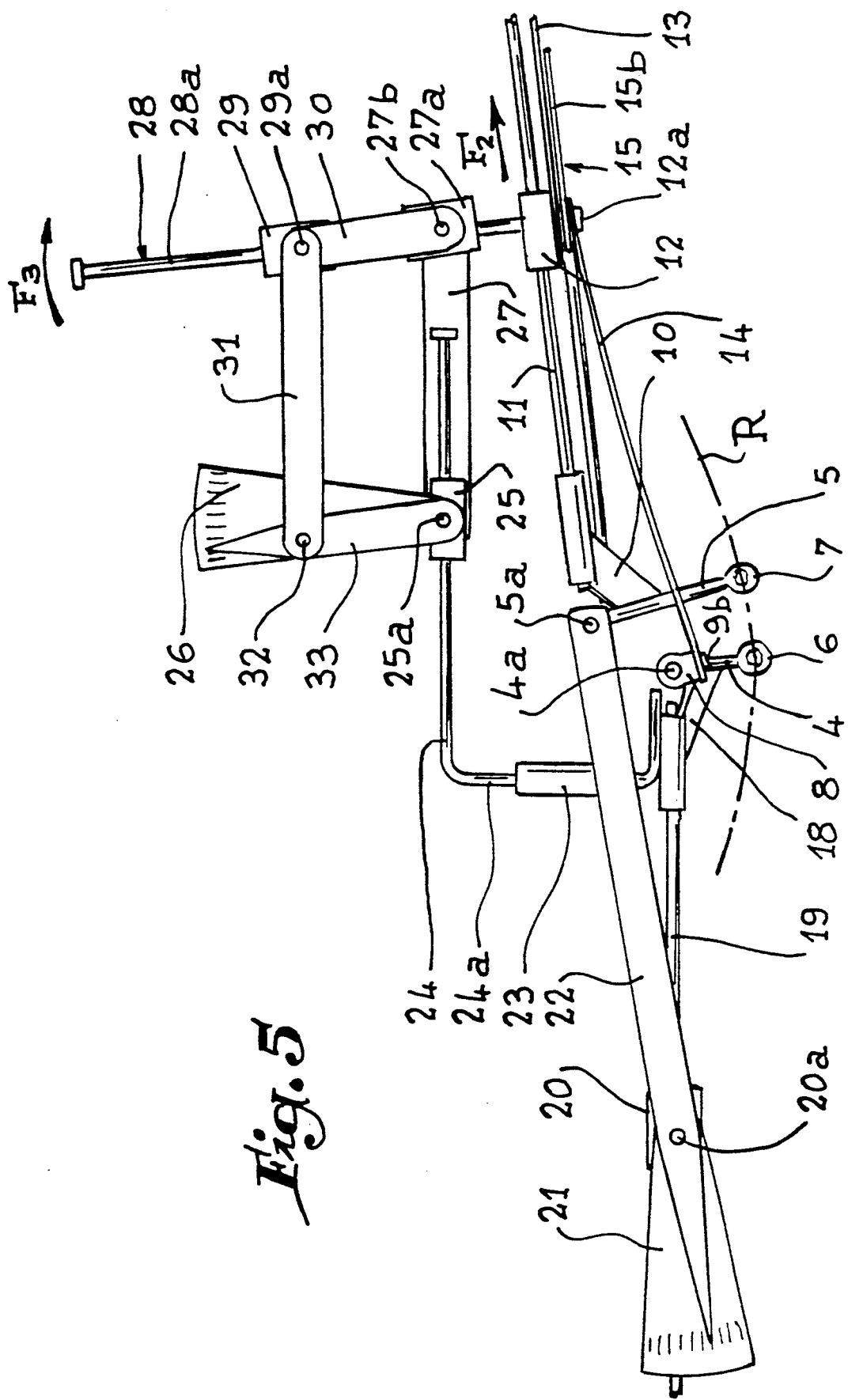
FIG. 5 is a view similar to that of FIG. 2, but illustrating the measurement of the angle of displacement of the two vertebrae in lateral inflexion from their position of FIG. 3.

If the vertebrae are displaced in lateral inflexion, i.e. giving axis X-Y a curvature in plane R, the two rods 4 and 5 effect complex rotations, so that, on the one hand, carriage 20 slides along rod 19 due to the spaced apart relationship of the two rods 4 and 5 and, on the other hand, rod 28 changes relative position with respect to rod 24, moving away from it in the direction of arrow F2 (FIG. 5), while tipping in the direction of arrow F3. Under these conditions, the deformable parallelogram 27, 30, 31, 33 is deformed and the end of the needle 33 moves with respect to the graduation of the dial 26 to indicate the maximum angle of clearance of the two vertebrae in lateral inflexion.

The maximum angle of rotation of one vertebra with respect to the other in plane Q may also be measured. The relative displacement of the two rods 4 and 5 in this plane Q, in the case of lateral flexion, causes the two ends 4a and 5a of the columns to move apart, which causes, on the one hand, movement of the carriage 20 on rod 19 and a subsequent rotation of the needle 22 whose end moves in front of the graduation of the dial 21 to indicate, for example, the maximum amplitude of freedom of the two vertebrae in the direction of the rotation.

Under these conditions, the utility of providing the supple connecting rods 14 and 17 so that they may follow without deformation the relative movements of the rods 4 and 5 in rotation and in lateral inflexion, will be understood.

Of course, proximity gauges or potentiometers may be provided at the pins 12a of carriage 12, 20a of carriage 20 and 25a of block 25 to measure the angles of clearance by means of an electronic converter with digital display or like apparatus to which the gauges or potentiometers would be connected.

Figure 6:
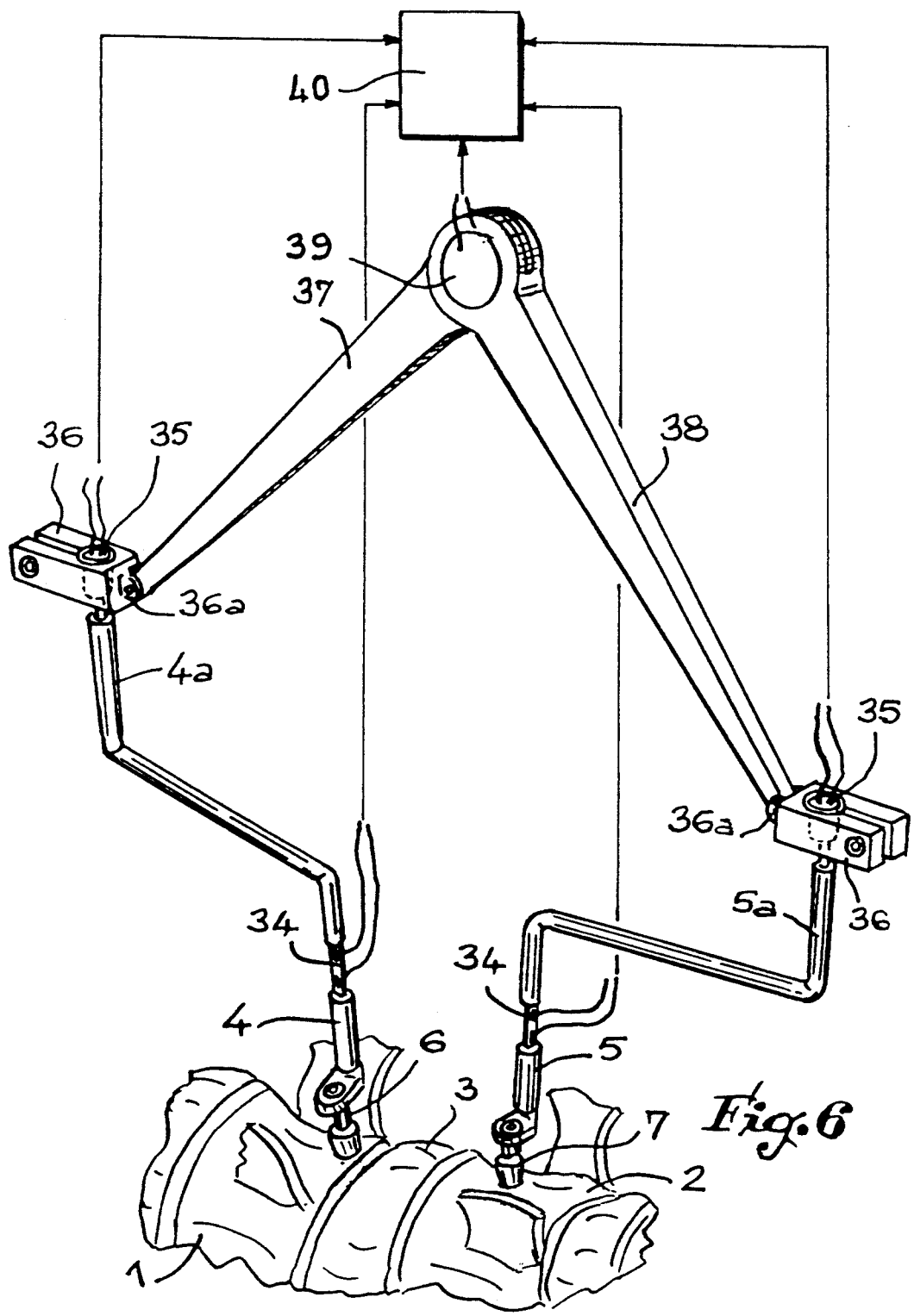
FIG. 6 is a perspective view of a variant embodiment of the device of FIG. 1.

FIG. 6 illustrates a variant embodiment of the measuring device according to the invention.

The device illustrated in FIGS. 1 to 6 allows the measurement of the angles of torsion, of lateral inflexion and of flexion-extension of adjacent vertebrae but without reference to the force applied on these vertebrae to displace them in the three directions mentioned above.

On the contrary, in accordance with the device of FIG. 6, it is possible to measure the angles of torsion and of flexion-extension of the vertebrae 1 and 2 as a function of the force exerted thereon via the rods 4 and 5 which each include a strain gauge 34. This gauge is placed in the vicinity of attachment of rods 4 and 5 with respect to the screws or implants 6, 7 connected to the vertebrae 1 and 2. Rods 4 and 5 are in fact constituted by rods bent twice as an S and which are disposed substantially in the plane P containing the longitudinal axis X-Y of the spine.

The ends 4a, 5a of the rods which are located substantially parallel to screws 6 and 7 bear at their ends a rotation monitoring gauge 35 adapted to rotate in a block 36. The opposite faces of the two blocks 36 each include a fork joint 36a in which is articulated one of the ends of a connecting rod 37, 38 respectively. The opposite end of the connecting rod 38 is secured to a rotation monitoring gauge 39 rotating with respect to a pin fixed to the corresponding end of the other connecting rod 37. In this way, rods 37 and 38 substantially form compasses of which the legs are displaced in plane P.

Gauges 34, 35 and 39 are connected to an electronic converter 40 with digital display adapted to display the angles of torsion and of flexion-extension of the vertebrae 1 and 2 as a function of the force applied thereon by displacing rods 4 and 5 either in torsion or in flexion-extension.

This measurement is therefore effected for example in torsion by displacing the two rods 4 and 5 in two opposite directions perpendicularly to plane P. This displacement provokes rotation of the rotation monitoring gauges 35 with respect to the blocks 36, the blocks remaining in plane P due to their link with connecting rods 37 and 38.

If it is desired to measure the angle of flexion-extension, rods 4, 5 are displaced in plane P in opposite direction, which provokes displacement of the two blocks 36, moving away from each other so that, in that case, it is gauge 39 which measures the variation of the angle of the connecting rods.

It goes without saying that the proximity gauges may be replaced by rotatable potentiometers without departing from the scope of the invention or by any other like device.

What is claimed is:

1. An apparatus for measuring an angle of movement of one vertebra of a patient with respect to another spaced vertebra relative to at least two of three orthogonal planes which extend through a longitudinal axis along which the vertebrae are aligned for purposes of making therapeutical decisions with respect to spinal surgical procedures, wherein the vertebrae include outwardly extending spinous processes and wherein the three orthogonal planes include a first plane extending along the longitudinal axis and in general alignment with the spinous processes, a second plane extending perpendicularly with respect to the longitudinal axis, and a third plane orthogonal to both the first and second planes and extending along the longitudinal axis, the apparatus comprising: an electrical converter and display means for indicating a degree of flexion-extensional movement in said first plane of the spaced vertebrae with respect to one another and indicating a degree of torsional movement of the spaced vertebrae with respect to one another in planes parallel to said second plane, first and second rods each having lower ends for engaging respective vertebrae in space relationship with respect to one another and each having upper ends, each of said rods including a strain gauge spaced intermediate said upper and lower ends, means for electrically connecting said strain gauge to said electrical converter and display means, a pair of first rotation monitoring gauges mounted in spaced relationship to each other on said upper ends of said rods a pair of spaced block members, a pair of additional rods each having first ends mounted in spaced relationship to one of said block members and each supporting said block members in surrounding relationship to one of said first rotation monitoring gauges, each of said additional rods having second ends which are pivotable about a joint with respect to one another, a second rotation monitoring gauge mounted to measure the relative rotation between said second ends of said additional rods, and means for electrically connecting each of said first and said second rotation monitoring gauges to said electrical convertor and display means whereby the degree of flexion-extensional movement of the spaced vertebrae relative to one another and the degree of torsional movement of the spaced vertebrae with respect to one another may be displayed when forces are applied on said first and second rods.

* * * * *